US 9,827,067 B2

(12) United States Patent
Iwasaki et al.

(10) Patent No.: US 9,827,067 B2
(45) Date of Patent: Nov. 28, 2017

(54) LINEAR MEMBER TRANSFER APPARATUS

(71) Applicant: OLYMPUS CORPORATION, Tokyo (JP)

(72) Inventors: Tomokazu Iwasaki, Hachioji (JP); Hideto Onishi, Hachioji (JP); Akihisa Ogawa, Hachioji (JP); Masahiko Tomita, Hachioji (JP); Young Chung Kim, Singapore (SG)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/592,271

(22) Filed: May 11, 2017

(65) Prior Publication Data

US 2017/0239016 A1     Aug. 24, 2017

Related U.S. Application Data

(63) Continuation of application No. PCT/JP2016/079865, filed on Oct. 6, 2016.

(30) Foreign Application Priority Data

Feb. 2, 2016   (JP) ................. 2016-018120

(51) Int. Cl.
    *B08B 9/043*     (2006.01)
    *A61B 90/70*     (2016.01)
(52) U.S. Cl.
    CPC ............ *A61B 90/70* (2016.02); *B08B 9/0436* (2013.01); *A61B 2090/701* (2016.02)

(58) Field of Classification Search
    CPC .. A61B 90/70; A61B 2090/701; B08B 9/0436
    See application file for complete search history.

(56) References Cited

U.S. PATENT DOCUMENTS

| 2007/0234495 A1* | 10/2007 | Suzuki ................. A61B 1/122 |
| | | 15/104.095 |
| 2009/0119856 A1* | 5/2009 | Onishi ................. A61B 90/70 |
| | | 15/104.066 |

FOREIGN PATENT DOCUMENTS

| JP | 2004-208961 A | 7/2004 |
| JP | 2007-260279 A | 10/2007 |
| JP | 2007-282674 A | 11/2007 |
| JP | 2015-181801 A | 10/2015 |

* cited by examiner

*Primary Examiner* — Randall Chin
(74) *Attorney, Agent, or Firm* — Scully, Scott, Murphy & Presser, P.C.

(57) ABSTRACT

A linear member transfer apparatus includes: a linear member housing portion having a bottomed cylindrical shape and including: a bottom portion; an opening; a side wall; a restriction portion that is a diaphragm disposed on a position at a predetermined distance from the bottom portion and that has an inner diameter smaller than an inner diameter of the bottom portion; a first chamber configured to house a linear member in a wound state; and a second chamber configured to house the linear member in an extended state; a transfer portion configured to transfer the linear member; and a guide.

9 Claims, 12 Drawing Sheets ns apparatus.

LINEAR MEMBER TRANSFER APPARATUS

CROSS REFERENCE TO RELATED APPLICATION

This application is a continuation application of PCT/JP2016/079865 filed on Oct. 6, 2016 and claims benefit of Japanese Application No. 2016-018120 filed in Japan on Feb. 2, 2016, the entire contents of which are incorporated herein by this reference.

BACKGROUND OF THE INVENTION

1. Field of the Invention

The present invention relates to a linear member transfer apparatus.

2. Description of the Related Art

Conventionally, there is an insertion object transfer apparatus for endoscope capable of inserting and removing a cleaning brush that is a linear member into and from an endoscope channel to allow cleaning the endoscope channel contaminated by use. For example, Japanese Patent Application Laid-Open Publication No. 2015-181801 discloses an insertion object transfer apparatus for endoscope capable of sending out a cleaning brush housed in a housing portion to an endoscope channel and capable of drawing the sent cleaning brush into the housing portion to wind and house the cleaning brush.

SUMMARY OF THE INVENTION

An aspect of the present invention provides a linear member transfer apparatus including: a linear member housing portion having a bottomed cylindrical shape and including: a bottom portion; an opening disposed on a position at a predetermined distance from the bottom portion; a side wall connecting the bottom portion and the opening; a restriction portion that is a diaphragm disposed on a position at a predetermined distance from the bottom portion and that has an inner width smaller than an inner width of the bottom portion; a first chamber formed by the bottom portion and the side wall, communicatively connected to the restriction portion, and configured to house a linear member in a wound state; and a second chamber formed by the opening and the side wall, communicatively connected to the restriction portion, and configured to house the linear member in an extended state; a transfer portion configured to transfer the linear member in a normal direction from the bottom portion toward the opening and in an opposite direction from the opening toward the bottom portion; and a guide connecting the transfer portion and the opening and formed to expand from the transfer portion toward the opening.

An aspect of the present invention provides a linear member transfer apparatus including: a linear member housing portion having a frustum shape and including: a bottom portion; a side wall, wherein an angle formed by the side wall and the bottom portion is smaller than 90 degrees; and an opening disposed on a distal end of the side wall and having an inner width smaller than an inner width of the bottom portion; and a transfer portion configured to transfer a linear member in a normal direction from the bottom portion toward the opening and in an opposite direction from the opening toward the bottom portion.

DETAILED DESCRIPTION OF THE PREFERRED EMBODIMENT(S)

Hereinafter, an embodiment of the present invention will be described with reference to the drawings.

Configuration

Figure 1:
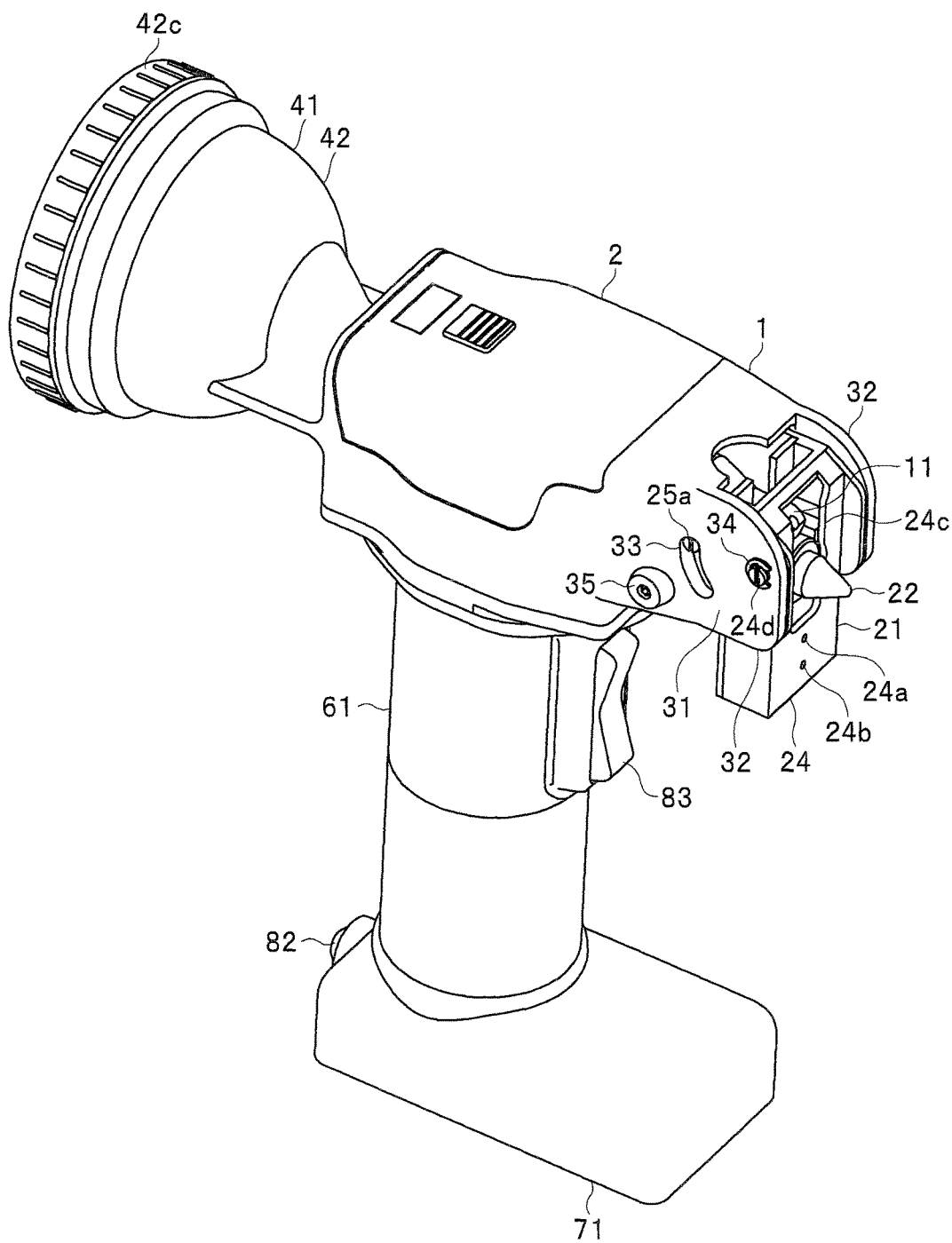
FIG. 1 is a perspective view showing an external configuration of a linear member transfer apparatus according to an embodiment of the present invention.

FIG. 1 is a perspective view showing an external configuration of a linear member transfer apparatus 1 according to the embodiment of the present invention.

Figure 2:
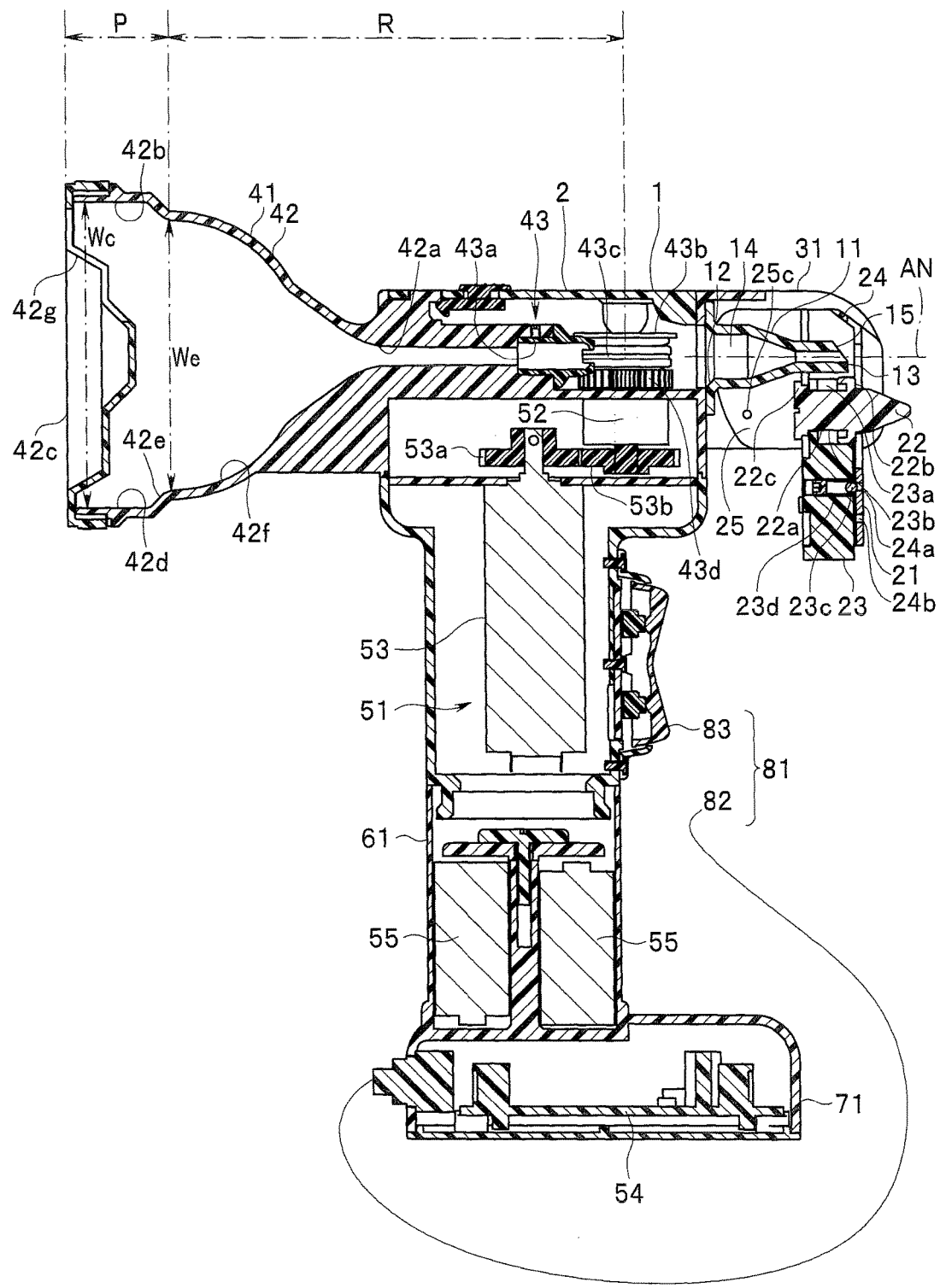
FIG. 2 is a cross-sectional view showing a configuration of the linear member transfer apparatus according to the embodiment of the present invention.
Figure 3:
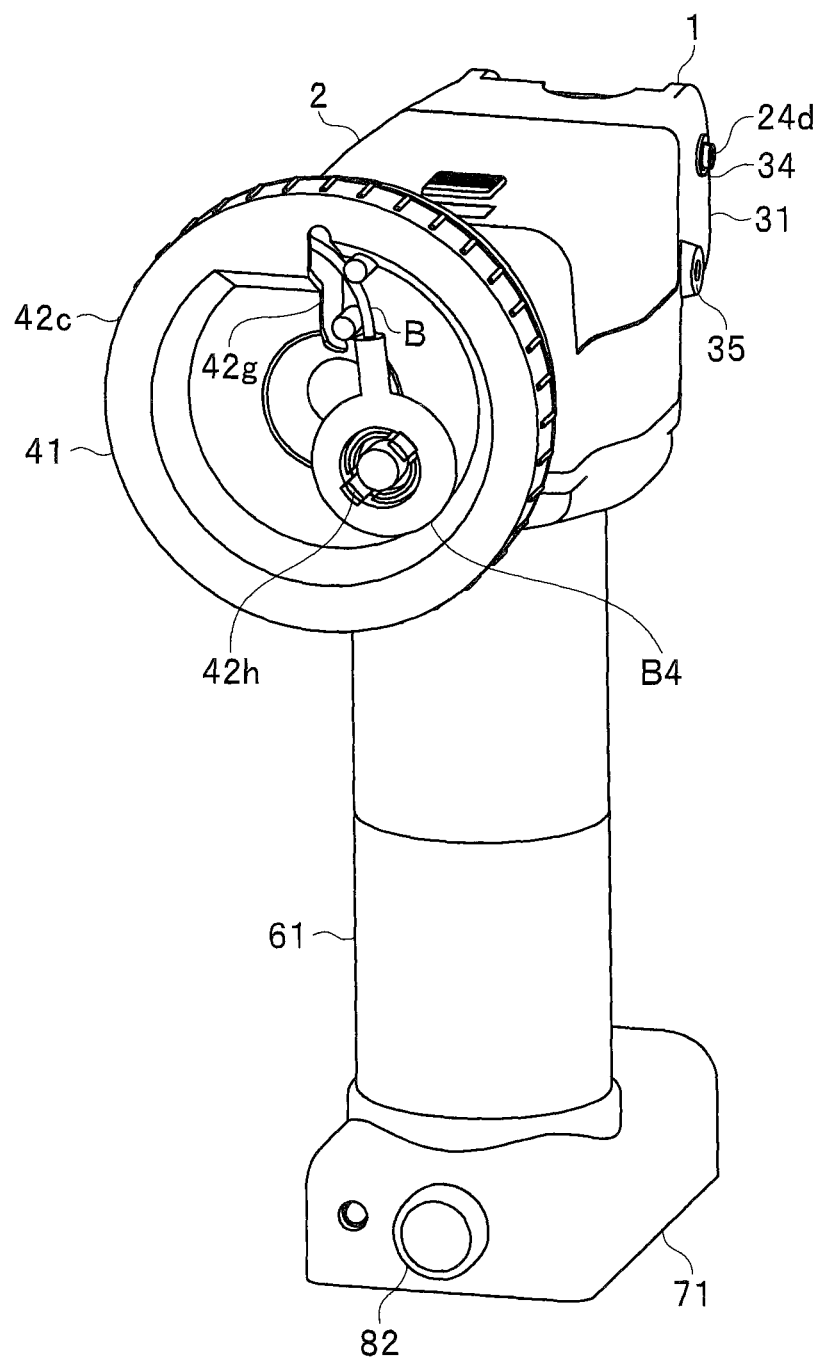
FIG. 3 is a rear perspective view showing an external configuration of the linear member transfer apparatus according to the embodiment of the present invention.
Figure 4:
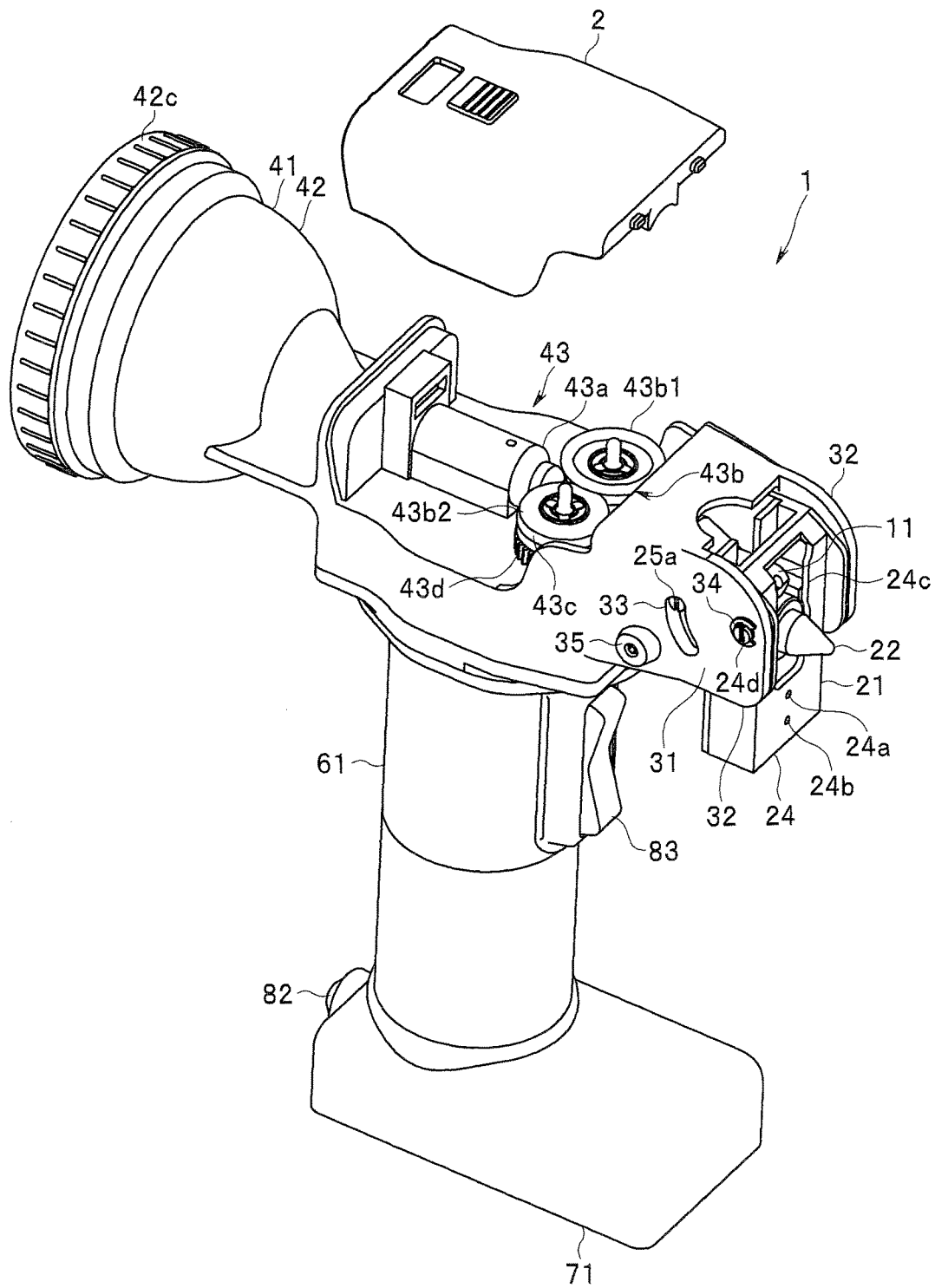
FIG. 4 is a perspective view showing an external configuration of a state in which a cover of the linear member transfer apparatus is removed according to the embodiment of the present invention.

FIG. 2 is a cross-sectional view showing a configuration of the linear member transfer apparatus 1 according to the embodiment of the present invention. FIG. 3 is a rear perspective view showing an external configuration of the linear member transfer apparatus 1 according to the embodiment of the present invention. FIG. 4 is a perspective view showing an external configuration of a state in which a cover 2 of the linear member transfer apparatus 1 is removed according to the embodiment of the present invention.

The linear member transfer apparatus 1 includes a nozzle 11, a fitting portion 21, a switching portion 31, a holding portion 41, a driving portion 51, a grasping portion 61, a pedestal portion 71, and an operation portion 81.

The nozzle 11 is configured to be able to send out a cleaning brush B described later to a suction cylinder side opening El (FIG. 7) of an endoscope E. The nozzle 11 is configured by, for example, plastic. The nozzle 11 includes an inlet port 12 for leading in the cleaning brush B, an outlet port 13 for leading out the cleaning brush B, and an insertion path 14 connecting the inlet port 12 and the outlet port 13. The insertion path 14 is formed in a cylindrical shape becoming narrower from the inlet port 12 toward the outlet port 13. The outlet port 13 is formed such that at least part of an end surface is inclined in a direction orthogonal to a central axis AN of the nozzle 11 to prevent the nozzle 11 from hitting a pipe sleeve E11 provided on the suction cylinder side opening El of the endoscope E when an angle of the nozzle 11 is switched. In the present embodiment, one side 15 of edges of the outlet port 13 is formed to incline in the direction orthogonal to the central axis AN of the nozzle 11.

The fitting portion 21 includes a fitting slit 24c described later and can be fitted to the pipe sleeve E11 in an outward flange shape of the endoscope E. When the fitting portion 21 is fitted to the pipe sleeve Eli, the outlet port 13 faces and opposes the pipe sleeve E11. The fitting portion 21 includes a connection guide 22, a slide piece 23, a case body 24, and extending plates 25.

The connection guide 22 is configured by, for example, plastic. In the connection guide 22, a body portion 22a is formed in a columnar shape, a distal end is formed to become narrower, and a shoulder portion 22b and a base portion 22c are formed in a brim shape. In the connection guide 22, a compression spring 23a is fitted onto the body portion 22a. When the connection guide 22 is attached to a hollow portion 23b provided on the slide piece 23, the compression spring 23a is pressed against the shoulder portion 22b, and the connection guide 22 is biased in a distal end direction of the connection guide 22. The base portion 22c is pressed against the case body 24, and this restricts projection of the connection guide 22 biased in the distal end direction.

The slide piece 23 is configured by, for example, plastic. The slide piece 23 is slidably fitted into the case body 24. The hollow portion 23b for attaching the connection guide 22 is provided on the slide piece 23. The slide piece 23 includes a ball plunger 23d including a ball 23c biased in a direction of pushing by the compression spring 23a.

The case body 24 is configured by, for example, metal. The case body 24 is fitted onto the slide piece 23. The case body 24 includes positioning holes 24a and 24b for fitting the ball 23c of the ball plunger 23d to allow switching a position of the slide piece 23 in a slide direction in two conditions. The case body 24 includes the fitting slit 24c to allow sliding and fitting with the pipe sleeve E11 of the endoscope E. The fitting slit 24c is formed such that the nozzle 11 and the connection guide 22 are exposed. The case body 24 includes a turning shaft 24d pivotally supported by the switching portion 31. The fitting portion 21 can turn about the turning shaft 24d.

The extending plates 25 respectively extend from both side portions of the case body 24 so as to be connected to the switching portion 31. Each of the extending plates 25 is provided with a pin 25a loosely fitted to a bent long hole 33 of the switching portion 31 to allow restricting a turning range of the fitting portion 21. Each of the extending plates 25 includes positioning holes 25b and 25c for fitting a ball not shown of a ball plunger 35 (described later) to allow switching a position of the fitting portion 21 in a turning direction in two conditions.

The switching portion 31 connects the fitting portion 21 and the nozzle 11 such that a crossing angle of the suction cylinder side opening El of the endoscope E and the central axis AN of the nozzle 11 switches to a plurality of angles in a state that the fitting portion 21 is fitted to the endoscope E.

The switching portion 31 is configured by, for example, plastic. The switching portion 31 includes two support plates 32 disposed to face each other across the fitting portion 21. Each of the two support plates 32 includes: a bearing hole 34 for pivotally supporting the turning shaft 24d of the fitting portion 21; the bent long hole 33 for restricting the turning range of the fitting portion 21; and the ball plunger 35 that can switch the turning angle of the fitting portion 21 in two conditions. As a result, the switching portion 31 can pivotally support the fitting portion 21 and switch the crossing angle of the suction cylinder side opening El of the endoscope E and the central axis AN of the nozzle 11 in two conditions.

The holding portion 41 is configured to be able to hold the cleaning brush B led out from the outlet port 13 of the nozzle 11. The holding portion 41 includes a linear member housing portion 42 and a connection portion 43.

The linear member housing portion 42 is configured to be able to house the cleaning brush B in a state in which the cleaning brush B is wound. The linear member housing portion 42 is configured by, for example, plastic. The linear member housing portion 42 includes a cylindrical side wall 42b becoming narrower toward an opening 42a, a round bottom portion 42c, a first chamber 42d, a restriction portion 42e, and a second chamber 42f. A guide 43a of the connection portion 43 is attached to the opening 42a.

The bottom portion 42c is configured by, for example, a cap that can be attached and detached. The bottom portion 42c includes a ring draw-out hole 42g and a ring hook 42h. As shown in FIG. 3, a ring B4 of the cleaning brush B is drawn out from the ring draw-out hole 42g of the bottom portion 42c and hooked on the ring hook 42h. Note that the bottom portion 42c may not include the ring draw-out hole 42g and the ring hook 42h.

The first chamber 42d is formed in a short cylindrical shape to allow bending the cleaning brush B along the side wall 42b to wind and house the cleaning brush B.

The restriction portion 42e is extended from the first chamber 42d and formed in a conical surface shape, becoming narrower toward the second chamber 42f. The restriction portion 42e is formed smaller than the bottom portion 42c and is provided on a position at a predetermined distance P from the bottom portion 42c. The cleaning brush B wound and housed in the first chamber 42d is pressed against the restriction portion 42e, and the restriction portion 42e restricts expansion of the cleaning brush B.

The second chamber 42f is extended from the restriction portion 42e and formed in a bottomed cylindrical shape becoming narrower toward the opening 42a such that the cleaning brush B comes out from the bottom portion 42c along an axial direction of the linear member housing portion 42 in a state in which the cleaning brush B is linearly extended.

P represents the predetermined distance from the bottom portion 42c to the restriction portion 42e of the linear member housing portion 42, and R represents a predetermined distance from the restriction portion 42e to a transfer portion described later. In that case, it is preferable that R is as long as or longer than P.

As for a ratio of the predetermined distance P and the predetermined distance R, the predetermined distance R is 1 or more when the predetermined distance P is 1, and it is more preferable that the predetermined distance R is 5 or more. When the predetermined distance P is 1, it is preferable that the predetermined distance R is 9 or less. That is, the ratio of the distance from the bottom portion 42c to the restriction portion 42e and the distance from the restriction portion 42e to a transfer portion 43b is 1:1 to 1:9. Note that when a transfer portion 43b includes a roller 43b as in FIG. 2, the predetermined distance R is a distance from the restriction portion 42e to a center of the roller 43b.

Figure 6:
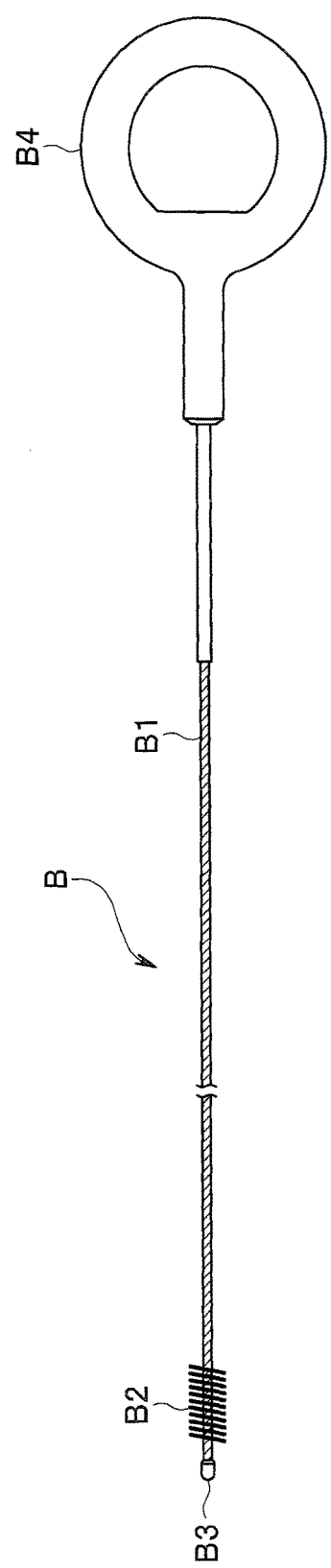
FIG. 6 is a diagram showing an example of a cleaning brush of the linear member transfer apparatus according to the embodiment of the present invention.

An inner diameter We of the bottom portion 42c is formed to be larger than an inner diameter We of the restriction portion 42e. It is desirable that a size of a difference in level configured by a difference between the inner diameter We of the restriction portion 42e and the inner diameter We of the bottom portion 42c is a size at least equal to or greater than a half of a maximum diameter of an applied linear member so that the expansion of the linear member can be restricted. For example, when a linear member including a shaft B1 part as shown in FIG. 6 is used, it is desirable that the difference in level is equal to or greater than a radius of the shaft B1.

That is, the linear member housing portion 42 has a bottomed cylindrical shape and includes: the round bottom portion 42c; the opening 42a disposed on a position at a predetermined distance from the bottom portion 42c; the side wall 42b connecting the bottom portion 42c and the opening 42a; the restriction portion 42e that is a diaphragm disposed on a position at the predetermined distance P from the bottom portion 42c and that has an inner diameter smaller than an inner diameter of the bottom portion 42c; the first chamber 42d formed by the bottom portion 42c and the side wall 42b, communicatively connected to the restriction portion 42e, and configured to house the cleaning brush B in a wound state; and the second chamber 42f formed by the opening 42a and the side wall 42b, communicatively connected to the restriction portion 42e, and configured to house the cleaning brush B in an extended state.

Note that although the bottom portion 42c is round in the present embodiment, the bottom portion 42c may not be round. The bottom portion 42c may be, for example, oval, elliptical, or polygonal.

The connection portion 43 is configured to connect the opening 42a of the linear member housing portion 42 and the inlet port 12 of the nozzle 11. The connection portion 43 includes the guide 43a and the roller 43b that is a transfer portion. As shown in FIG. 4, the cover 2 that can be attached and detached is provided above the connection portion 43 so as to cover the connection portion 43, and the cover 2 can be removed to expose the connection portion 43.

The guide 43a is provided between the roller 43b and the opening 42a of the linear member housing portion 42 and connects the roller 43b and the opening 42a. The guide 43a is formed to become narrower from the opening 42a toward the roller 43b, in other words, to expand from the roller 43b toward the opening 42a. The guide 43a can house a brush B2 (FIG. 6) on a distal end of the cleaning brush B, and the guide 43a guides the cleaning brush B coming out to the roller 43b. It is desirable that an inner diameter of the guide 43a is larger than an outer diameter of the brush B2 to prevent bristles of the brush B2 from falling down.

The roller 43b that is the transfer portion can be rotated and driven to transfer the cleaning brush B in a normal direction from the bottom portion 42c toward the opening 42a and in an opposite direction from the opening 42a toward the bottom portion 42c. The roller 43b is configured by a driving roller 43b1 and a driven roller 43b2 disposed to face each other. Each of the driving roller 43b1 and the driven roller 43b2 includes an anti-slip rubber ring 43c on an outer circumference. The driving roller 43b1 is linked to a drive shaft 52 of the driving portion 51 and is rotated and driven by the driving portion 51. Each of the driving roller 43b1 and the driven roller 43b2 includes two gears 43d engaged with each other on a proximal end. The driving roller 43b1 transmits rotational force to the driven roller 43b2 through the two gears 43d and rotates the driven roller 43b2 in a direction opposite the driving roller 43b1.

Figure 5:
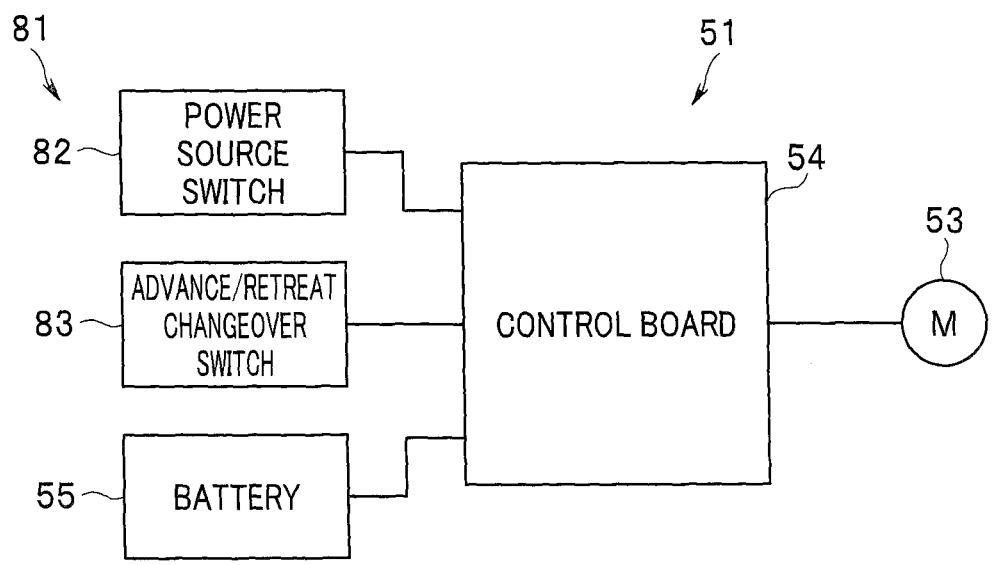
FIG. 5 is an explanatory view describing a configuration of a driving portion and an operation portion of the linear member transfer apparatus according to the embodiment of the present invention.

FIG. 5 is an explanatory view describing a configuration of the driving portion 51 and the operation portion 81 of the linear member transfer apparatus 1 according to the embodiment of the present invention.

As shown in FIG. 5, the driving portion 51 includes a motor 53, a control board 54, and a battery 55.

The motor 53 transmits rotation force to a gear 53a attached to a motor shaft, a gear 53b engaged with the gear 53a, the drive shaft 52 linked to the gear 53b, and the driving roller 43b1 linked to the drive shaft 52. The motor 53 is provided in the grasping portion 61. The motor 53 is connected to the control board 54. The motor 53 rotates and drives the roller 43b under the control of the control board 54.

The control board 54 includes a circuit configured to control the rotation of the motor 53. The control board 54 is provided in the pedestal portion 71. The control board 54 is connected to the battery 55 and the operation portion 81. The control board 54 causes the motor 53 to rotate according to an instruction input inputted through the operation portion 81.

The battery 55 supplies electric power to the motor 53 under the control of the control board 54.

The operation portion 81 includes a power source switch 82 and an advance/retreat switch 83. The operation portion 81 is connected to the control board 54. When there is an instruction input for the operation portion 81, the instruction input is outputted to the control board 54.

The power source switch 82 is configured to be able to input an instruction for ON/OFF switch of a power source.

The advance/retreat switch 83 is configured to be able to input an instruction for advance and retreat of the cleaning brush B, that is, sending out and drawing in the cleaning brush B.

Subsequently, the cleaning bush B housed in the linear member transfer apparatus 1 and sent out from the linear member transfer apparatus 1 will be described.

FIG. 6 is a diagram showing an example of the cleaning brush B of the linear member transfer apparatus 1 according to the embodiment of the present invention.

The cleaning brush B includes the shaft B1, the brush B2, a distal end tip B3, and the ring B4.

The shaft B1 is formed into an elongated shape by tightly winding a thin metal wire into a coil shape. The shaft B1 is inserted into an endoscope channel and has a length enough for the brush B2 provided on the distal end to rub and pass through the endoscope channel to clean the endoscope channel. The shaft B1 is provided with restoring force to return to a linear shape. The shaft B1 may be deformed in advance, or external force may be applied in advance to the shaft B1, to provide appropriate restoring force. For example, the shaft B1 may be curled or may be softened by external force.

The brush B2 is provided on the distal end of the shaft B1. The brush B2 is formed in a size that allows the brush B2 to pass through the endoscope channel while rubbing the endoscope channel. Note that in place of the brush B2, another member, such as sponge and rubber, which can pass through the endoscope channel while rubbing the endoscope channel may be provided.

The distal end tip B3 is provided on the distal end of the shaft B1 to allow the roller 43b to easily draw in the cleaning brush B.

The ring B4 is provided on a back end of the shaft B1 and can be hooked on the ring hook 42h of the holding portion 41. Note that the ring B4 may not be provided.

When the cleaning brush B is drawn into the linear member housing portion 42 by the rotation of the roller 43b, the shaft B1 is sequentially bent along the side wall 42b of the linear member housing portion 42, and the shaft B1 is housed in the linear member housing portion 42 in the wound state. In other words, variability of the winding state of the cleaning brush B can be restricted to an extent that does not obstruct the sending and drawing of the cleaning brush B.

Coming-out force of the cleaning brush B presses the distal end tip B3 against the roller 43b, and the brush B2 is disposed in the guide 43a.

Action

Subsequently, action of the linear member transfer apparatus 1 will be described.

Figure 7:
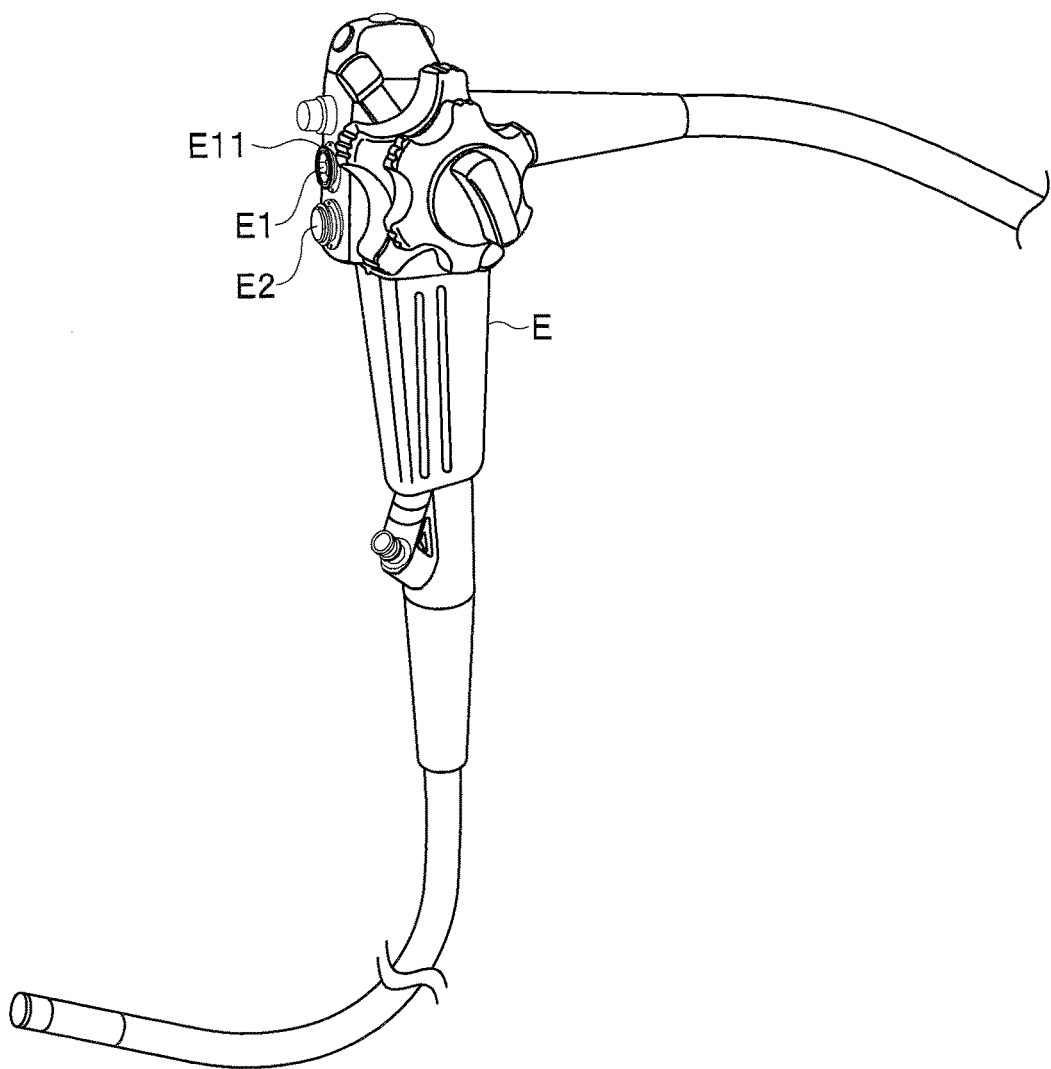
FIG. 7 is a diagram showing an example of an external configuration of an endoscope provided with the linear member transfer apparatus according to the embodiment of the present invention.
Figure 8:
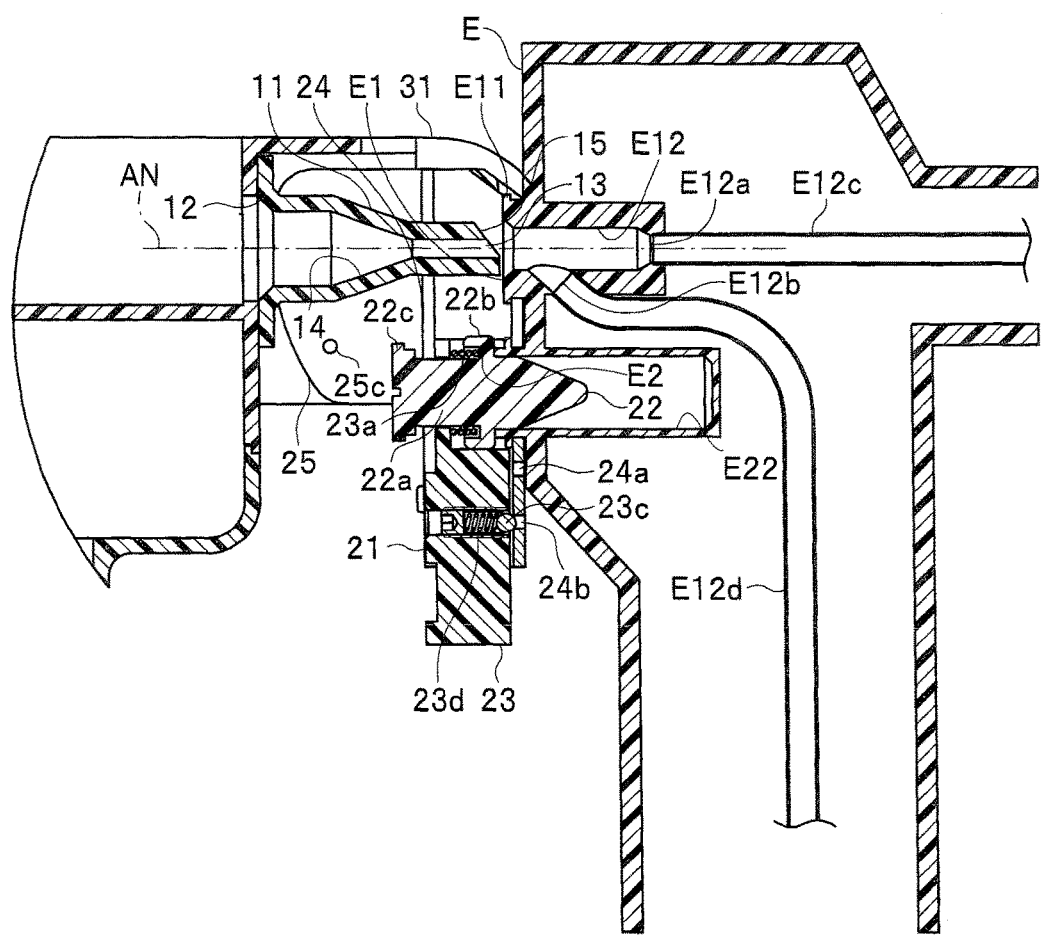
FIG. 8 is an explanatory view describing a state in which a nozzle of the linear member transfer apparatus is directed toward a universal cord side channel according to the embodiment of the present invention.
Figure 9:
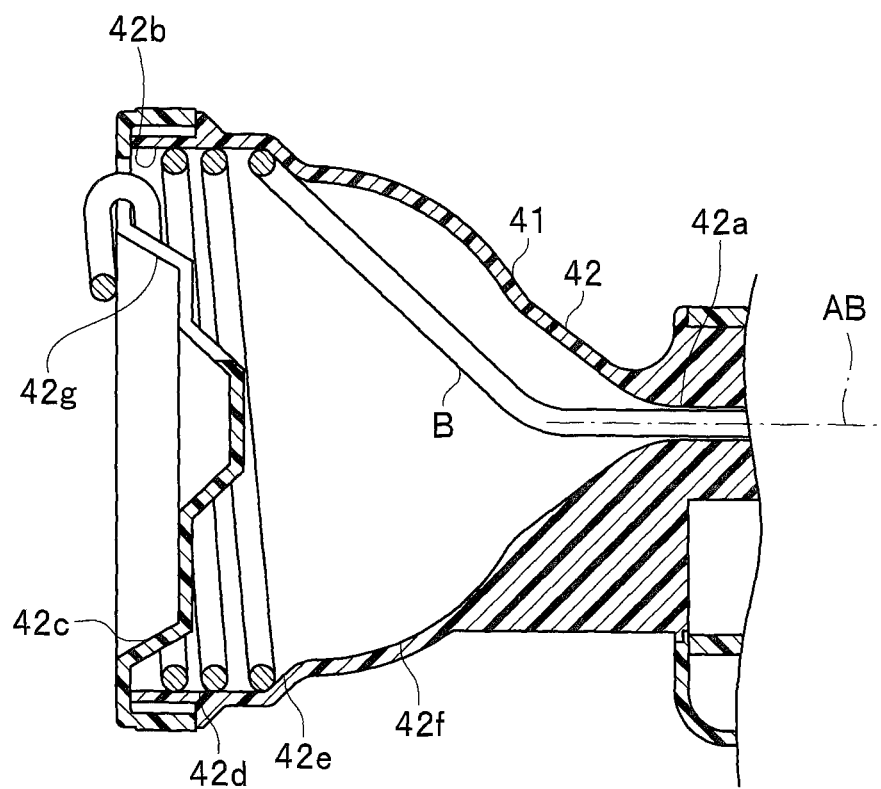
FIG. 9 is an explanatory view describing a state in which the cleaning brush is housed in a linear member housing portion of the linear member transfer apparatus according to the embodiment of the present invention.
Figure 10:
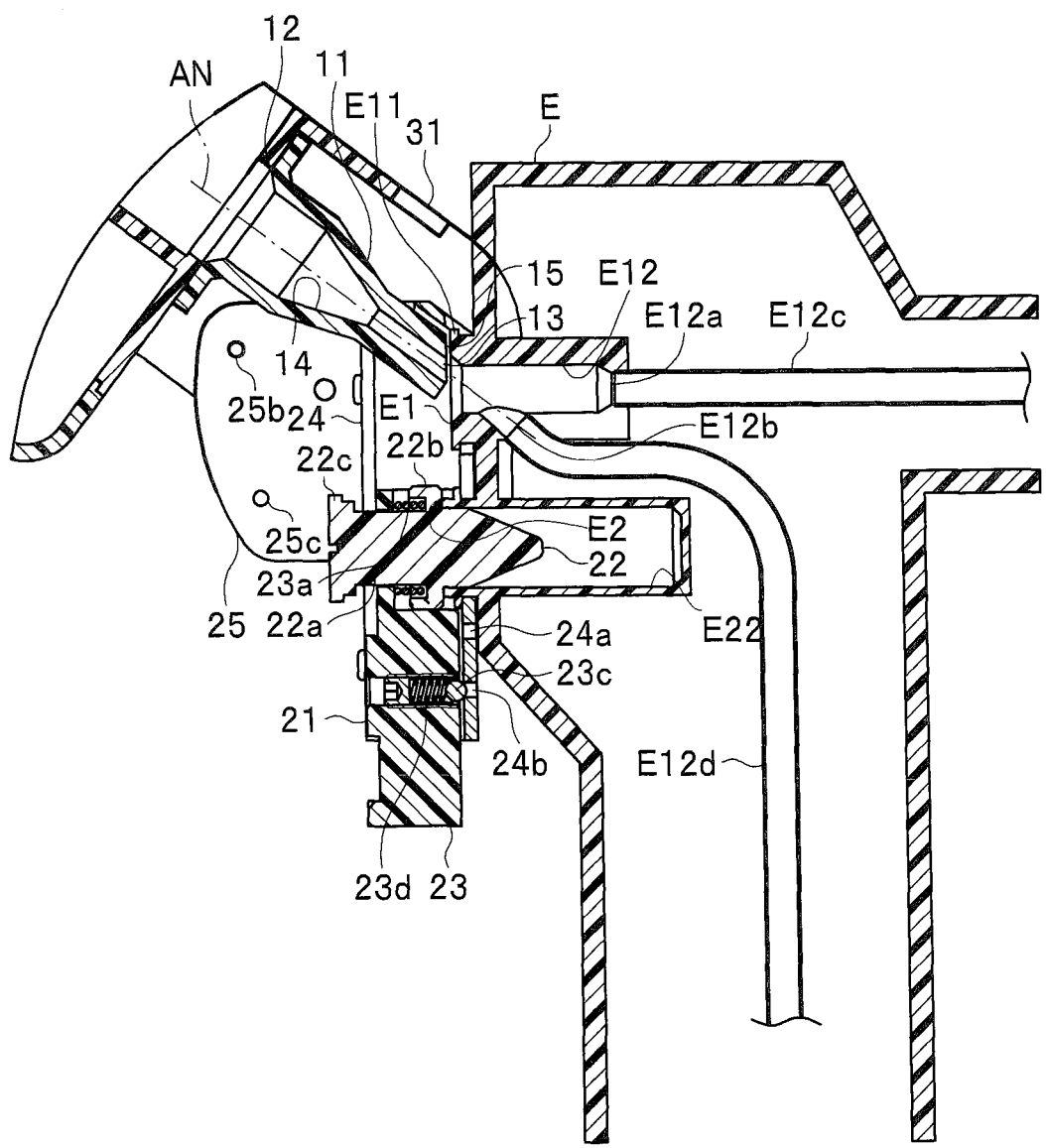
FIG. 10 is an explanatory view describing a state in which the nozzle of the linear member transfer apparatus is directed toward an insertion tube side channel according to the embodiment of the present invention.

FIG. 7 is a diagram showing an example of an external configuration of the endoscope E provided with the linear member transfer apparatus 1 according to the embodiment of the present invention. FIG. 8 is an explanatory view describing a state in which the nozzle 11 of the linear member transfer apparatus 1 is directed toward a universal cord side channel E12c according to the embodiment of the present invention. FIG. 9 is an explanatory view describing a state in which the cleaning brush B is housed in the linear member housing portion 42 of the linear member transfer apparatus 1 according to the embodiment of the present invention. FIG. 10 is an explanatory view describing a state in which the nozzle 11 of the linear member transfer apparatus 1 is directed toward an insertion tube side channel E12d according to the embodiment of the present invention.

As shown in FIG. 7, the endoscope E includes the suction cylinder side opening E1 and an air/water cylinder side opening E2. A suction cylinder E12 is formed in a cylindrical shape and includes a universal cord side opening E12a and an insertion tube side opening E12b inside. An air/water cylinder E22 is formed in a cylindrical shape and connected to an air feeding channel and a water feeding channel not shown.

As shown in FIG. 8, when the connection guide 22 is inserted into the air/water cylinder E22, an edge of the air/water cylinder side opening E2 is pressed against the shoulder portion 22b of the connection guide 22. Consequently, the shoulder portion 22b of the connection guide 22 rises against the biasing force of the compression spring 23a, and the pipe sleeve E11 of the suction cylinder E12 enters the inside of the case body 24 of the fitting portion 21 from the fitting slit 24c. Subsequently, when the endoscope E is slid in a direction from the suction cylinder E12 toward the air/water cylinder E22, the slide piece 23 is slid along with the connection guide 22 inserted into the endoscope E, and the ball 23c of the ball plunger 23d is fitted to the positioning hole 24b and positioned. As a result, the pipe sleeve E11 of the suction cylinder E12 is slid and fitted to the case body 24, and the nozzle 11 is directed toward the universal cord side opening E12a in the suction cylinder E12.

When the power source is put into an ON state by the power source switch 82, and an instruction for sending out the cleaning brush B is inputted by the advance/retreat switch 83, the instruction input is inputted to the control board 54. The control board 54 applies a current to the motor 53 to rotate the motor 53 and rotate the roller 43b. Consequently, the roller 43b draws in the distal end tip B3 of the cleaning brush B pressed against the roller 43b by the coming-out force. The roller 43b transfers the shaft B1 of the cleaning brush B to the nozzle 11 and sends out the cleaning brush B from the nozzle 11. The sent cleaning brush B enters the universal cord side channel E12c from the universal cord side opening E12a and rubs and cleans the inside of the universal cord side channel E12c.

When an instruction for drawing in the cleaning brush B is inputted by the advance/retreat switch 83, the control board 54 rotates the motor 53 in a direction opposite the direction in which the cleaning brush B is sent out. When the motor 53 is rotated, the roller 43b draws in the shaft B1 of the cleaning brush B. As shown in FIG. 9, the drawn shaft B1 of the cleaning brush B passes through the second chamber 42f and the restriction portion 42e and reaches the first chamber 42d. The shaft B1 is sequentially bent along the side wall 42b of the linear member housing portion 42 and housed in the first chamber 42d in the wound state. The shaft B1 housed in the first chamber 42d is pressed against the restriction portion 42e when the shaft B1 is about to expand due to the restoring force, and the expansion of the shaft B1 is restricted. When the distal end tip B3 of the cleaning brush B passes through the roller 43b, the drawing in of the cleaning brush B is completed. As a result, the cleaning brush B is housed in the first chamber 42d with low variability of winding diameter and winding position. In other words, the variability of the winding state of the cleaning brush B can be restricted to an extent that does not obstruct the sending out or drawing in of the cleaning brush B.

To clean the insertion tube side channel E12d, the fitting portion 21 is turned, and the nozzle 11 is directed toward the insertion tube side opening E12b to send out the cleaning brush B as shown in FIG. 10. After the insertion tube side channel E12d is cleaned, the cleaning brush B is housed in the first chamber 42d in the wound state.

The restriction portion 42e restricts the expansion of the shaft B1 housed in the linear member housing portion 42 in the wound state when the shaft B1 is about to expand due to the restoring force to return to the linear shape, and the variability of the winding diameter and the winding position is low.

The shaft B1 presses the bottom portion 42c by the restoring force, and coming-out force from the opening 42a is generated by the reaction force against the bottom portion 42c, which pushes out the cleaning brush B. The restoring force varies according to a degree of curvature of the shaft B1, and the coming-out force also varies according to the degree of curvature of the shaft B1. However, the variability of the winding diameter and the winding position is low, and the coming-out force is stable.

The coming-out force is always applied to the roller 43b during the sending and drawing. Therefore, a load applied to the roller 43b is stabilized by stabilizing the coming-out force, and as a result, the sending-out and drawing-out operation can also be stabilized.

According to the embodiment, when the cleaning brush B is stored in the linear member housing portion 42, the distal end tip B3 is pressed against the roller 43b by the coming-out force of the cleaning brush B. Therefore, when the cleaning brush B is drawn in, a length of drawing in the cleaning brush B does not have to be worried about, and the cleaning brush B can be drawn in until the distal end tip B3 passes the roller 43b.

According to the embodiment, the cleaning brush B restricted by the restriction portion 42e is housed in the first chamber 42d in the linear member transfer apparatus 1. The coming-out force of the cleaning brush B coming out from the linear member housing portion 42 is stabilized, and the roller 43b can stably send out the cleaning brush B.

First Modification of Embodiment

In the embodiment, the side wall 42b of the restriction portion 42e is formed in a conical surface shape, becoming narrower from the first chamber 42d side toward the second chamber 42f side. However, a separate diaphragm in a bowl shape may be attached.

Figure 11:
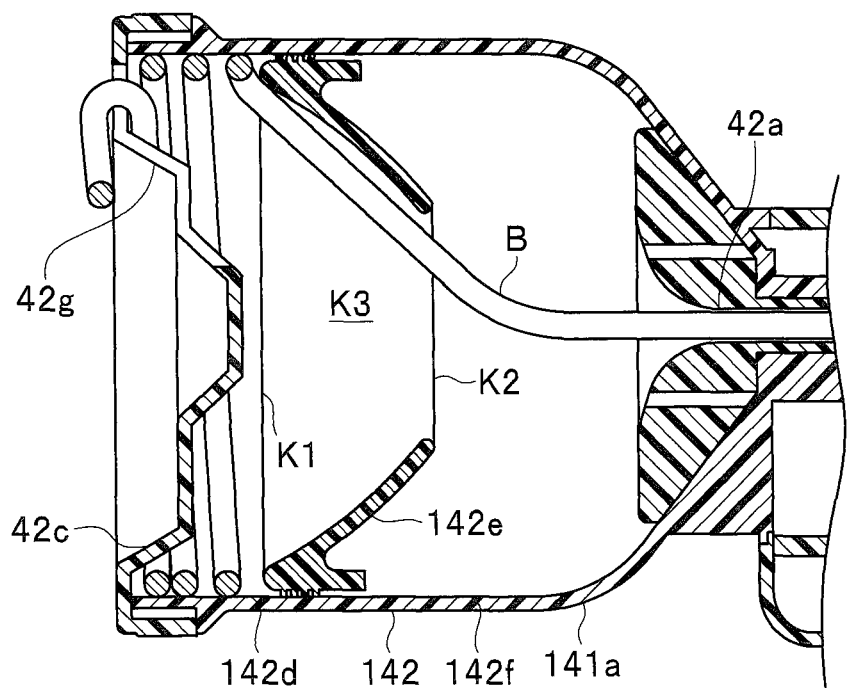
FIG. 11 is an explanatory view describing a state in which the cleaning brush is housed in a linear member housing portion of the linear member transfer apparatus according to a first modification of the embodiment of the present invention.

FIG. 11 is an explanatory view describing a state in which the cleaning brush B is housed in a linear member housing portion 142 of the linear member transfer apparatus 1 according to a first modification of the embodiment of the present invention. In the description of the first modification of the embodiment, the same components as in the embodiment are provided with the same reference signs, and the description will not be repeated.

In the linear member housing portion 142, a shoulder portion 141a is round, and the linear member housing portion 142 is formed in a bottomed cylindrical shape becoming narrower from the shoulder portion 141a toward the opening 42a.

A restriction portion 142e is attached between a first chamber 142d and a second chamber 142f. The restriction portion 142e includes a first chamber side opening K1, a second chamber side opening K2 smaller than the bottom portion 42c and the first chamber side opening K1, and a side wall K3 connecting the first chamber side opening K1 and the second chamber side opening K2. The side wall K3 is formed by a round surface narrowed down in a bowl shape from the first chamber 142d side toward the second chamber 142f side.

According to the first modification of a first embodiment, the cleaning brush B restricted by the restriction portion 142e in the bowl shape is housed in the first chamber 142d in the linear member transfer apparatus 1. The coming-out force of the cleaning brush B coming out from the linear member housing portion 142 is stabilized, and the roller 43b can stably send out the cleaning brush B.

Second Modification of Embodiment

In the embodiment, the side wall 42b of the restriction portion 42e is formed in a conical surface shape, becoming narrower from the first chamber 42d side toward the second chamber 42f side. However, a diaphragm in a ring shape may be attached to form the side wall 42b.

Figure 12:
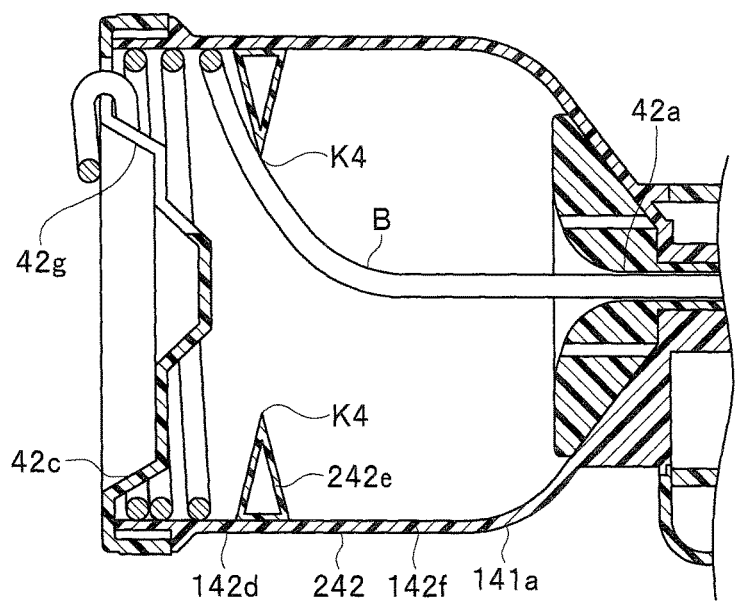
FIG. 12 is an explanatory view describing a state in which the cleaning brush is housed in a linear member housing portion of the linear member transfer apparatus according to a second modification of the embodiment of the present invention.

FIG. 12 is an explanatory view describing a state in which the cleaning brush B is housed in a linear member housing portion 242 of the linear member transfer apparatus 1 according to a second modification of the embodiment of the present invention. In the description of the second modification of the embodiment, the same components as in the embodiment are provided with the same reference signs, and the description will not be repeated.

In the linear member housing portion 242, the shoulder portion 141a is round, and the linear member housing portion 242 is formed in a bottomed cylindrical shape becoming narrower from the shoulder portion 141a toward the opening 42a.

A restriction portion 242e is a diaphragm formed in a ring shape and is attached between the first chamber 142d and the second chamber 142f. An inner circumference K4 of the restriction portion 242e is formed smaller than the bottom portion 42c.

According to the second modification of the first embodiment, the cleaning brush B restricted by the restriction portion 242e in the ring shape is housed in the first chamber 142d in the linear member transfer apparatus 1. The coming-out force of the cleaning brush B coming out from the linear member housing portion 242 is stabilized, and the roller 43b can stably send out the cleaning brush B.

Third Modification of Embodiment

In the embodiment, the first modification of the embodiment, and the second modification of the embodiment, the linear member housing portion 42 includes the first chamber 42d, the restriction portion 42e, and the second chamber 42f. However, the first chamber, the restriction portion, and the second chamber may be configured by an integrated conical surface.

Figure 13:
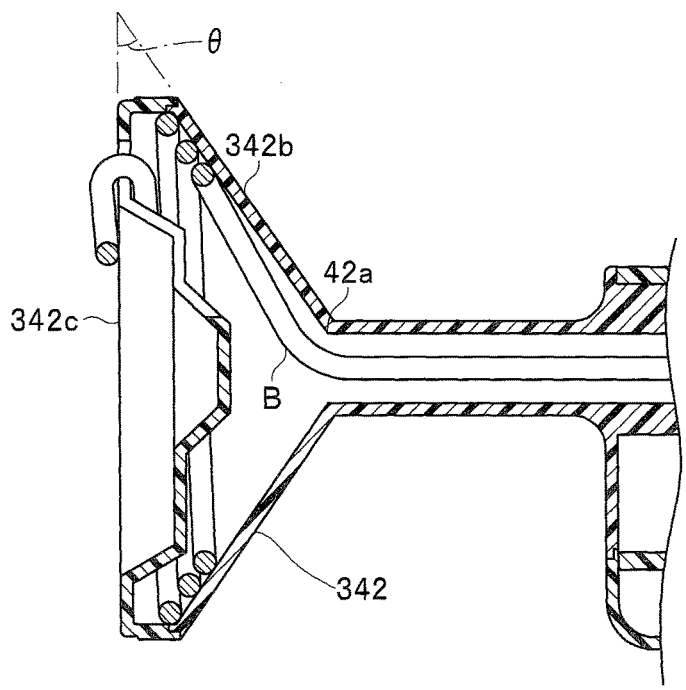
FIG. 13 is an explanatory view describing a state in which the cleaning brush is housed in a linear member housing portion of the linear member transfer apparatus according to a third modification of the embodiment of the present invention.

FIG. 13 is an explanatory view describing a state in which the cleaning brush B is housed in a linear member housing portion 342 of the linear member transfer apparatus 1 according to a third modification of the embodiment of the present invention. In the description of the third modification of the embodiment, the same components as in the embodiment are provided with the same reference signs, and the description will not be repeated.

The linear member housing portion 342 has a frustum shape and includes: a bottom portion 342c; a side wall 342b, wherein an angle A formed by the side wall 342b and the bottom portion 342c is smaller than 90 degrees, more preferably, smaller than 60 degrees; and the opening 42a disposed on a distal end of the side wall 342b and having an inner width smaller than an inner width of the bottom portion 342c.

According to the third modification of the embodiment, the cleaning brush B housed in the linear member housing portion 342 is restricted by the side wall 342b in the linear member transfer apparatus 1. The coming-out force of the cleaning brush B coming out from the linear member housing portion 42 is stabilized, and the roller 43b can stably send out the cleaning brush B.

Note that although the example in which the linear member is the cleaning brush B is described in the embodiment, the linear member is not limited to the cleaning brush B. For example, the linear member may be a treatment instrument, such as a cytology brush, a guide wire, and a catheter.

The present invention is not limited to the embodiment, and various changes, modifications, and the like can be made without departing from the scope of the present invention.

According to the present invention, a linear member transfer apparatus capable of stabilizing coming-out force of a linear member coming out from a linear member housing portion and stably sending out the linear member can be provided.

What is claimed is:

1. A linear member transfer apparatus comprising:
   a linear member housing portion having a bottomed cylindrical shape and comprising:
   a bottom portion;
   an opening disposed on a position at a predetermined distance from the bottom portion;
   a side wall connecting the bottom portion and the opening;
   a restriction portion that is a diaphragm disposed on a position at a predetermined distance from the bottom portion and that has an inner width smaller than an inner width of the bottom portion;
   a first chamber formed by the bottom portion and the side wall, communicatively connected to the restriction portion, and configured to house a linear member in a wound state; and
   a second chamber formed by the opening and the side wall, communicatively connected to the restriction portion, and configured to house the linear member in an extended state;
   a transfer portion configured to transfer the linear member in a normal direction from the bottom portion toward the opening and in an opposite direction from the opening toward the bottom portion; and
   a guide connecting the transfer portion and the opening and formed to expand from the transfer portion toward the opening.

2. The linear member transfer apparatus according to claim 1, wherein the transfer portion includes at least one roller.

3. The linear member transfer apparatus according to claim 1, wherein a ratio of a distance from the bottom portion to the restriction portion and a distance from the restriction portion to the transfer portion is 1:1 to 1:9.

4. The linear member transfer apparatus according to claim 1, further comprising
   the linear member, wherein
   a difference in level between the inner width of the restriction portion and the inner width of the bottom portion is equal to or greater than a radius of the linear member.

5. The linear member transfer apparatus according to claim 1, wherein
   the bottom portion is formed in a round shape.

6. The linear member transfer apparatus according to claim 1, wherein
   the guide houses a brush on a distal end of the linear member.

7. The linear member transfer apparatus according to claim 1, wherein
   the linear member transfer apparatus can transfer the linear member to an endoscope channel, and
   the linear member is a cleaning brush of an endoscope.

8. A linear member transfer apparatus comprising:
   a linear member housing portion having a frustum shape and comprising:
   a bottom portion;
   a side wall, wherein an angle formed by the side wall and the bottom portion is smaller than 90 degrees; and
   an opening disposed on a distal end of the side wall and having an inner width smaller than an inner width of the bottom portion; and
   a transfer portion configured to transfer a linear member in a normal direction from the bottom portion toward the opening and in an opposite direction from the opening toward the bottom portion.

9. The linear member transfer apparatus according to claim 8, wherein
   the linear member housing portion has a frustoconical shape.

* * * * *